US00PP17891P2

(12) United States Plant Patent
Korlipara

(10) Patent No.: US PP17,891 P2
(45) Date of Patent: Jul. 31, 2007

(54) ***VERBASCUM* PLANT NAMED 'ROYALTY'**

(50) Latin Name: ***Verbascum* hybrid**
Varietal Denomination: Royalty

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/343,467

(22) Filed: Jan. 30, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman LLP

(57) ABSTRACT

A new and distinct *Verbascum* plant characterized by numerous deep reddish purple colored flowers on numerous short, upright flowering stems, a compact habit, and excellent vigor.

1 Drawing Sheet

Botanical denomination: *Verbascum* hybrid ((*V. phoeniceum*×*dumulosum*)×*V. phoeniceum*)).

Variety designation: 'Royalty'.

The present invention relates to a new and distinct cultivar of *Verbascum* hybrid, and given the cultivar name 'Royalty'. *Verbascum* is in the family Scrophulariaceae.

This new cultivar originated from a controlled cross in a cultivated area between *Verbascum* 'Jackie', an unpatented plant, as the seed parent and *Verbascum phoeniceum* purple, an unpatented plant grown from seed, as the pollen parent. *Verbascum* 'Jackie' is an unpatented plant that originated from a cross between *Verbascum phoeniceum* and *Verbascum dumulosum*.

This new *Verbascum* hybrid is unique in its deep purple flower color combined with its very compact habit and very short, multiple flowering stems.

This plant is characterized by the following:

1. Large deep reddish purple flowers.
2. Numerous upright, branching flowering stems.
3. Compact habit.
4. Very short flowering stems.
5. Excellent vigor.

This new cultivar has been reproduced only by asexual propagation (tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows three one-year-old plants of *Verbascum* 'Royalty' in bloom in early summer. These were planted together in a 1½ gallon pot and grown in a greenhouse.

DETAILED PLANT DESCRIPTION

The following is a detailed description of the new *Verbascum* based on observations of a one-year-old specimen grown outside in the ground in full sun in the trial fields in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on the Royal Horticultural Society Colour Chart.

Plant:

*Type.*—Herbaceous perennial.
*Form.*—Clumping basal rosette.
*Hardiness.*—U.S.D.A. Hardiness Zones 5-9.
*Size.*—10 cm tall and 19 cm wide, not including inflorescence.
*Vigor.*—Excellent.
*Roots.*—With one main tap root, and many fibrous lateral branches, White 155A.
*Stem.*—6 crowns, with each stem much congested, 6 mm wide and deep with no space between the internodes.

Leaf:

*Type.*—Simple, evergreen.
*Arrangement.*—Basal.
*Shape.*—Ovate.
*Blade size.*—8 cm long and 6.2 cm wide.
*Venation.*—Pinnate.
*Margins.*—Crenate.
*Apex.*—Acute.
*Base.*—Cuneate.
*Surface texture.*—Pubescent on both sides.
*Petiole.*—Grows to 1 cm long and 7 mm wide, stellate, Yellow Green 145D.
*Leaf color.*—Top side — Yellow Green 147A with main vein, Yellow Green 145D. Bottom side — Yellow Green 147B.

Inflorescence:

*Type.*—Panicle.
*Total panicle size.*—34 cm high and 11 cm wide (where flowers are).
*Number of panicles per plant.*—6 in the first flush.
*Cauline leaves.*—1 to 3 in number, 1.5 to 3 cm long and 0.7 to 1.5 cm wide.
*Flower number.*—Average count of 80 flowers on one panicle.

*Peduncle.*—Grows to 36 cm tall and 5 mm wide (near the base), glandular, Green 137C.

*Pedicel.*—Grows to 8 mm long, glandular, Green 137C.

*Bloom time.*—June to July in Canby, Oreg.

Flower bud:

*Size.*—10 mm wide and 6 mm deep.

*Description.*—Pentagonal cushion.

*Surface.*—Glandular hairs.

*Color.*—Purple 79A.

Flower:

*Type.*—Perfect, complete, irregular.

*Shape.*—Rotate, irregular, short tubular.

*Size.*—3.5 cm wide and 1.5 cm deep.

*Color.*—Purple 77A on the top and bottom sides.

*Corolla.*—Five lobes each, cut more than half way, each rhomboid, obtuse, entire, cupping back from mid line. Size — 3.5 cm wide and 1.5 cm deep because the lobes fold back. Surface — glabrous on both sides.

*Calyx.*—Shape — campanulate. Lobe number — 5, cut almost to the base, ovate, entire, acute tips. Size — 6 mm wide and 6 mm deep. Surface texture — Glandular hairs on inside and back side. Color — Green 137C on both sides.

*Stamens.*—Number — 5. Filaments — 1 cm long, top three with Yellow Orange 17A at base and bearded Purple 79A in the middle and White 155A on the top. The lower two filaments are Greyed Red 178A bearded Purple 79A on the lower ⅔. Anthers — Kidney shaped, 1 mm wide, Greyed Yellow 162A on bottom half and Greyed Purple 187A on top half. Pollen — Yellow Orange 23A.

*Pistil.*—One in number, 1.3 cm long. Style — Style 11 mm long and very narrow, Red Purple 59A. Ovary — Orbicular, Yellow Green 145B. Stigma — Yellow Green 147B.

*Fragrance — None.*

Fertility: Sterile, no fruit or seed produced.

Disease and pests: *Verbascum* are susceptible to fungal leaf spots and root rots. They need good drainage. Caterpillars may be a problem. This new cultivar has no known new resistance to any of these.

COMPARISONS

This new cultivar is similar in growth habit and flowering habit to *Verbascum* 'Jackie' (unpatented). *Verbascum* 'Jackie' has copper colored buds, which open to pale peach colored flowers and lavender stamens. This new cultivar has deep purple buds that open to deep reddish purple flowers. *Verbascum* 'Royalty' the same good qualities of numerous flowering stems, short flowering stems, but with an even more compact habit than *Verbascum* 'Jackie'.

Compared to *Verbascum* 'Sugar Plum' (U.S. Plant Pat. No. 16,224), the new cultivar is smaller overall with flowers that are deeper purple in color.

Compared to the pollen parent *Verbascum phoeniceum* purple, the new cultivar has more numerous and much shorter flowering stems, more leaves and crowns, and larger flowers.

I claim:

1. A new and distinct *Verbascum* plant as herein illustrated and described.

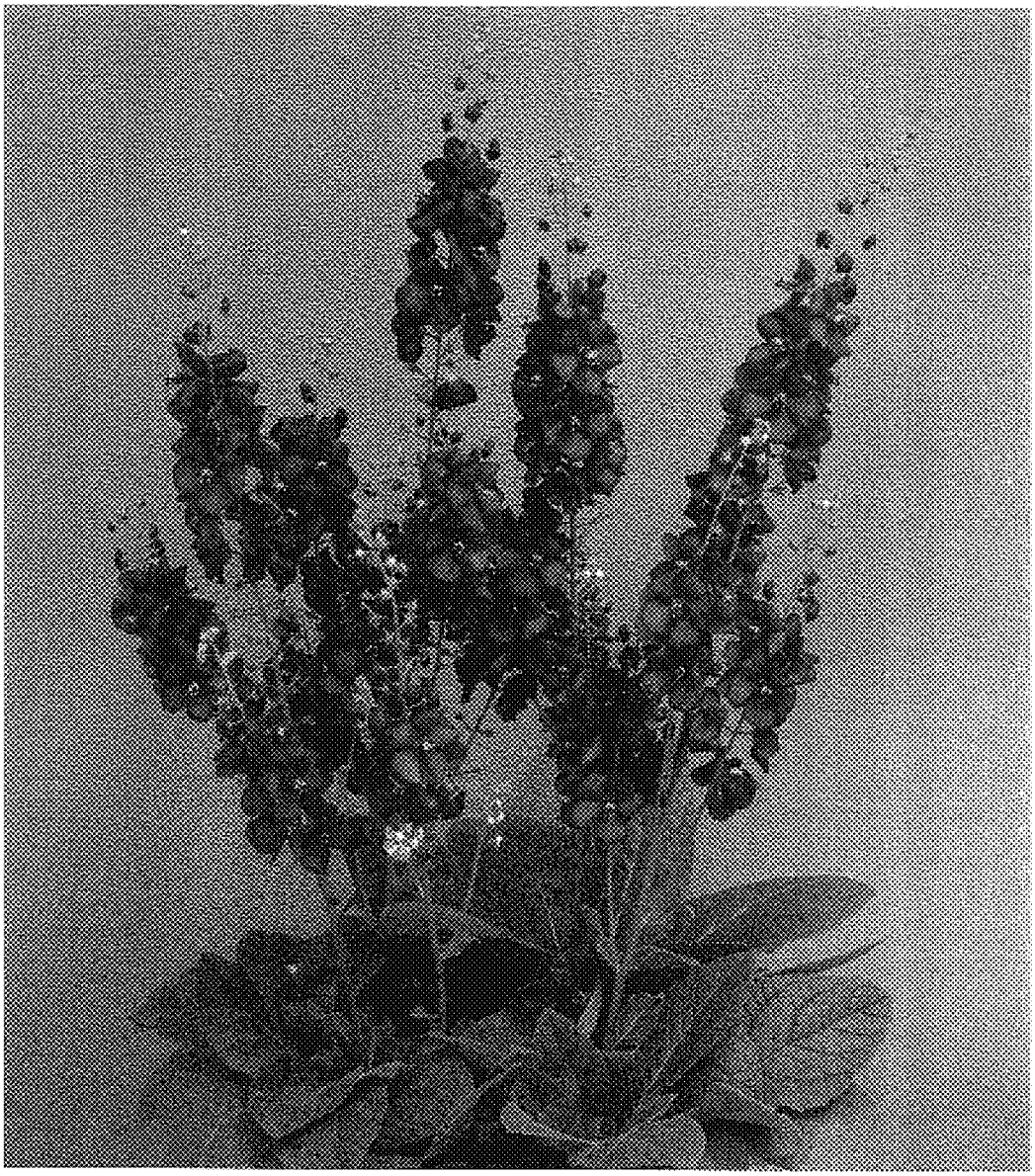

* * * * *